(12) United States Patent
Koduri et al.

(10) Patent No.: US 9,330,239 B2
(45) Date of Patent: May 3, 2016

(54) CLOUD-BASED INITIATION OF CUSTOMIZED EXERCISE ROUTINE

(71) Applicant: ZSOLUTIONZ, LLC, Sammamish, WA (US)

(72) Inventors: Sunil Koduri, Sammamish, WA (US); Bobby Joe Adams, Kirkland, WA (US); Surendra P. S. Bhatia, Kent, WA (US); John Michael Hand, Sammamish, WA (US); Shalini Koduri, Sammamish, WA (US); John W. Ransone, Wimberley, TX (US)

(73) Assignee: Zsolutionz, LLC, Sammamish, WA (US)

( * ) Notice: Subject to any disclaimer, the term of this patent is extended or adjusted under 35 U.S.C. 154(b) by 0 days.

(21) Appl. No.: 14/588,361

(22) Filed: Dec. 31, 2014

(65) Prior Publication Data

US 2015/0199494 A1 Jul. 16, 2015

Related U.S. Application Data

(60) Provisional application No. 61/927,359, filed on Jan. 14, 2014.

(51) Int. Cl.
  *A63F 13/12* (2006.01)
  *G06F 19/00* (2011.01)

(52) U.S. Cl.
  CPC .................................. *G06F 19/3481* (2013.01)

(58) Field of Classification Search
  USPC .............................................. 463/42; 700/91
  See application file for complete search history.

(56) References Cited

U.S. PATENT DOCUMENTS

| | | |
|---|---|---|
| D296,385 S | 6/1988 | Lenihan |
| D348,356 S | 7/1994 | Nemoto |
| D350,135 S | 8/1994 | Polk, Jr. et al. |

(Continued)

FOREIGN PATENT DOCUMENTS

| | | |
|---|---|---|
| EP | 0569879 A2 | 11/1993 |
| EP | 1758040 | 2/2007 |

(Continued)

OTHER PUBLICATIONS

Bauknecht, "We test it—The New Precor Adaptive Motion Trainer", Northwest Runner, Oct. 2013, pp. 14-15.

(Continued)

*Primary Examiner* — Pierre E Elisca
(74) *Attorney, Agent, or Firm* — Lee & Hayes, PLLC (57) ABSTRACT

Disclosed herein are techniques and systems for recognizing a user via a networked fitness system and initiating a customized exercise routine for the recognized user. The process includes receiving, at the networked fitness system, identification data associated with the user, and transmitting the identification data over a network to one or more remotely located servers. The networked fitness system may receive a user identification (ID) from the remotely located server(s) at least partly in response to the transmitted identification data, and receive a confirmation from the user that the user ID corresponds to the user. At least partly in response to the confirmation, the networked fitness system may automatically download a customized exercise routine associated with the user from the remotely located server(s) and initiate the customized exercise routine by the networked fitness system.

20 Claims, 6 Drawing Sheets

(56) References Cited

U.S. PATENT DOCUMENTS

| | | |
|---|---|---|
| 5,368,532 A | 11/1994 | Farnet |
| 5,527,239 A | 6/1996 | Abbondanza |
| 5,810,747 A | 9/1998 | Brudny et al. |
| 5,947,868 A | 9/1999 | Dugan |
| 6,126,572 A | 10/2000 | Smith |
| 6,152,856 A | 11/2000 | Studor et al. |
| D470,785 S | 2/2003 | Vermillion |
| 6,605,038 B1 | 8/2003 | Teller et al. |
| D531,989 S | 11/2006 | Dayan |
| D542,959 S | 5/2007 | Yao |
| 7,359,121 B2 | 4/2008 | French et al. |
| D584,843 S | 1/2009 | Kosche |
| D593,426 S | 6/2009 | Huang et al. |
| D619,485 S | 7/2010 | Ikeda et al. |
| D629,549 S | 12/2010 | Feigenbaum |
| 7,914,420 B2 | 3/2011 | Daly et al. |
| D636,769 S | 4/2011 | Wood et al. |
| D637,751 S | 5/2011 | Chiu |
| 8,007,405 B2 | 8/2011 | Burnfield et al. |
| D650,357 S | 12/2011 | Chen |
| 8,152,695 B2 | 4/2012 | Riley et al. |
| 8,235,724 B2 | 8/2012 | Gilley et al. |
| D678,271 S | 3/2013 | Chiu |
| D684,968 S | 6/2013 | Smith et al. |
| 8,537,568 B2 | 9/2013 | Tang |
| D693,325 S | 11/2013 | Lee |
| 8,597,142 B2 | 12/2013 | Mayles et al. |
| 8,620,146 B1 | 12/2013 | Coleman |
| D702,206 S | 4/2014 | Kim et al. |
| D702,232 S | 4/2014 | Choi |
| D705,777 S | 5/2014 | Groene et al. |
| D706,773 S | 6/2014 | Lu |
| D710,349 S | 8/2014 | Han et al. |
| D711,258 S | 8/2014 | Jacobs et al. |
| D711,871 S | 8/2014 | Daniel |
| 8,803,888 B2 | 8/2014 | Buban |
| D712,400 S | 9/2014 | Kim et al. |
| D712,855 S | 9/2014 | Thompson et al. |
| D712,899 S | 9/2014 | Park et al. |
| D712,946 S | 9/2014 | Hong |
| D714,746 S | 10/2014 | Euiseok et al. |
| D714,782 S | 10/2014 | Ohshima |
| D715,795 S | 10/2014 | McManigal |
| D716,265 S | 10/2014 | Park et al. |
| D716,293 S | 10/2014 | Hwang et al. |
| D716,799 S | 11/2014 | Green et al. |
| D718,303 S | 11/2014 | Choteau et al. |
| D720,334 S | 12/2014 | Wang |
| 2002/0055418 A1 | 5/2002 | Pyles et al. |
| 2003/0109322 A1 | 6/2003 | Funk et al. |
| 2004/0102931 A1 | 5/2004 | Ellis et al. |
| 2005/0039541 A1 | 2/2005 | Kurono |
| 2005/0070809 A1 | 3/2005 | Acres |
| 2005/0272561 A1* | 12/2005 | Cammerata ........ A63B 23/0494 482/8 |
| 2007/0123389 A1 | 5/2007 | Martin |
| 2007/0232452 A1 | 10/2007 | Hanoun |
| 2008/0300521 A1 | 12/2008 | Karkanias et al. |
| 2008/0300914 A1 | 12/2008 | Karkanias et al. |
| 2009/0069156 A1 | 3/2009 | Kurunmaki et al. |
| 2009/0156363 A1 | 6/2009 | Guidi et al. |
| 2010/0280416 A1 | 11/2010 | Hyde et al. |
| 2010/0323846 A1 | 12/2010 | Komatsu et al. |
| 2011/0016120 A1 | 1/2011 | Haughay, Jr. et al. |
| 2011/0172060 A1 | 7/2011 | Morales et al. |
| 2011/0201476 A1 | 8/2011 | Solomon |
| 2012/0109013 A1 | 5/2012 | Everett et al. |
| 2012/0122529 A1 | 5/2012 | Lyons |
| 2012/0139727 A1 | 6/2012 | Houvener et al. |
| 2012/0183939 A1 | 7/2012 | Aragones et al. |
| 2012/0220428 A1 | 8/2012 | Carlson |
| 2012/0251079 A1 | 10/2012 | Meschter et al. |
| 2012/0299846 A1 | 11/2012 | Matsuda |
| 2012/0310971 A1* | 12/2012 | Tran ........................ A63F 13/06 707/769 |
| 2012/0311334 A1* | 12/2012 | Bruestle .................. H04L 12/44 713/169 |
| 2013/0024408 A1* | 1/2013 | Firminger ................ G06N 5/02 706/17 |
| 2013/0090749 A1 | 4/2013 | Oswald et al. |
| 2013/0144411 A1 | 6/2013 | Savarese et al. |
| 2013/0178960 A1 | 7/2013 | Sheehan et al. |
| 2013/0225370 A1 | 8/2013 | Flynt et al. |
| 2013/0274066 A1 | 10/2013 | Ashby et al. |
| 2013/0307816 A1 | 11/2013 | Lee et al. |
| 2014/0249429 A1* | 9/2014 | Tran .................... A61B 5/0022 600/483 |
| 2014/0309082 A1 | 10/2014 | Iglehart |
| 2015/0196804 A1 | 7/2015 | Koduri et al. |
| 2015/0196805 A1 | 7/2015 | Koduri et al. |

FOREIGN PATENT DOCUMENTS

| | | |
|---|---|---|
| EP | 1978497 | 10/2008 |
| WO | WO9421171 A1 | 9/1994 |
| WO | WO2008007856 A1 | 1/2008 |
| WO | WO2013034987 A2 | 3/2013 |

OTHER PUBLICATIONS

Mulrooney, "How to Use My Polar Heart Rate Monitor With Life Fitness Equipment", retrieved from <<http://www.livestrong.com/article/223981-how-to-use-my-polar-heart-rate-monitor-with-life-fitness-equipment/>>, Sep. 2, 2010, 7 pages.

Octane Fitness, "Pro4700 Operations Manual", retrieved on Oct. 21, 2013 from <<http://www.octanefitness.com/files/octane/filemgmt/files/pro4700-operations-manual-.pdf, 24 pages.

Ursu, "10-Step Guide: How to Use the Weigh Loss Preset Treadmill Workouts", retrieved on Dec. 19, 2013 from <<http://www.performbetter.com/webapp/wcs/stores/servlet/PBOnePieceView?storeId=10151&pagename=283, 3 pages.

Waters, "Benefits of Training With Heart Rate Control", retreieved on Dec. 19, 2013 from <<www.smoothfitness.com/fitness-center/articles/training-with-heart-rate-control.htm>>, Smooth Fitness, 2 pages.

Office Action for U.S. Appl. No. 29/479,299, mailed on Jan. 7, 2015, Sunil Koduri, "Fitness Machine User Interface", 7 pages.

PCT Search Report and Written Opinion mailed Apr. 24, 2015 for PCT application No. PCT/US2014/072857, 9 pages.

PCT Search Report and Written Opinion mailed May 11, 2015 for PCT Application No. PCT/US14/72854, 15 Pages.

PCT Search Report and Written Opinion mailed Apr. 24, 2015 for PCT application No. PCT/US2014/072849, 12 pages.

Shu, et al., "In-Shoe Plantar Pressure Measurement and Analysis System Based on Fabric Pressure Sensing Array", retrieved from <<http://repository.lib.polyu.edu.hk/jspui/bitstream/103971252711105378500.pdf>>, IEEE Transactions on Information Technology in Biomedicine, vol. 14, No. 3, May 2010, 9 pages.

Office Action for U.S. Appl. No. 14/588,289, mailed on Jul. 22, 2015, Sunil Koduri, "Sensor-Based Evaluation and Feedback of Exercise Performance", 21 pages.

Office Action for U.S. Appl. No. 14/588,346, mailed on Oct. 16, 2015, Sunil Koduri, "Fuzzy Logic-Based Evaluation and Feedback of Exercise Performance", 9 pages.

* cited by examiner

CLOUD-BASED INITIATION OF CUSTOMIZED EXERCISE ROUTINE

CROSS REFERENCE TO RELATED APPLICATIONS

This application is based on and claims priority to U.S. Provisional Application No. 61/927,359, filed on Jan. 14, 2014, entitled, "CLOUD-BASED INITIATION OF CUSTOMIZED EXERCISE ROUTINE," the contents of which are herein incorporated by reference.

BACKGROUND

Exercise is necessary to maintain both physical and mental health. Although many people prefer exercising outdoors, it is often difficult to do so due to potentially adverse weather conditions and/or unsuitable urban environments. Accordingly, many individuals have taken to exercising indoors in places such as at health clubs, gyms, or even their own home (e.g., a room or garage) where environmental conditions are controllable and predictable. In these settings, weight lifting equipment may be used to improve one's muscular strength, while fitness machines (e.g., treadmills, elliptical machines, stationary bicycles, etc.) may be used for cardiovascular exercise.

Despite the advantages provided by fitness machines, today's fitness machines are limited in what they can do for a user. For example, fitness machines are predominantly "manual" in design. Namely, each time a user begins a workout on a fitness machine, he/she typically provides input data (e.g., weight, age, etc.), and selects a workout program or routine from multiple available routines (e.g., steady pace, interval training, hills, etc.). The available workout routines are often poorly tailored to the specific user of the fitness machine, making it more difficult for users to achieve fitness-related goals given the limited, manual input available on the fitness machine.

Current fitness machines are further limited in the feedback they can provide to the user. That is, any performance-related feedback provided by the fitness machine is generally limited to basic vital information (e.g., heart rate information) of the user. In such a scenario, a user is left to decide for themselves whether he/she should adjust the intensity (e.g., resistance, speed, etc.) of the workout program in an effort to achieve a target heart rate. Moreover, sensing mechanisms are limited to metal handgrips and heart monitoring chest straps configured to measure heart rate and other limited health measurements.

Furthermore, using fitness machines can also be rather boring and monotonous due to the unchanging scenery of most indoor environments. To cure this boredom, users typically listen to music or watch video media while exercising on a fitness machine. However, the novelty of such passive media can eventually wear off, leading to continued boredom while exercising on a fitness machine.

SUMMARY

Described herein are techniques and systems for recognizing a user via a networked fitness system and initiating a customized exercise routine for the recognized user. The system may include a networked (network-enabled) fitness machine or other suitable devices or components with access to one or more remotely located servers. The system may obtain customized exercise routines and other information about a user from the remotely located server(s) in order to facilitate access to customized workouts and user profiles for users that are located at any location. In this sense, the networked fitness system and the remotely located servers constitute a distributed platform (i.e., a combination of software and hardware components) that provides a complete fitness experience for users of the platform. The system may obtain identification data associated with the user, and may transmit the identification data to the remotely located server(s) where a user identification (ID) may be located. The user may confirm the user ID to verify that the user ID located by the remotely located server(s) is correct. In this manner, the system may automatically download an exercise routine(s) that is customized to the specific user. The customized exercise routine may have been determined using fitness information in a fitness knowledge store, fuzzy logic, and similar technology to prescribe an optimal exercise regimen for the user.

In some embodiments, a process of recognizing a user via a networked fitness system to initiate a customized exercise routine includes receiving, at the networked fitness system, identification data associated with the user, and transmitting the identification data to one or more remotely located servers. A user identification (ID) may then be received from the remotely located server(s) at least partly in response to the transmitting of the identification data. The fitness system may receive a confirmation from the user that the user ID corresponds to the user, and at least partly in response to the confirmation, a customized exercise routine associated with the user may be automatically downloaded from the remote server(s). The networked fitness system may initiate the customized exercise routine that was downloaded.

In some embodiments, a networked fitness system includes one or more processors and one or more memories maintaining modules executable by the one or more processors, the modules comprising: an identification module to receive identification data associated with the user and cause transmission of the identification data over a network to one or more remotely located servers, an authorization module to receive a user ID from the remote server(s) at least partly in response to the transmission of the identification data, and receive a confirmation from the user that the user ID corresponds to the user, and a download module to automatically download, at least partly in response to receiving the confirmation, a customized exercise routine associated with the user from the one or more remotely located servers. The networked fitness system may be configured to initiate the downloaded exercise routine for the user.

The networked fitness system of the embodiments disclosed herein leverages a cloud-based infrastructure to provide user access to customized exercise routines from anywhere a networked fitness system is, or can be, disposed. The cloud-based infrastructure provides a platform where users can experience a customized fitness program that is tailored to the particular user. In this manner, the platform may help a user achieve results and goals quickly and efficiently by allowing easy access to a prescribed workout regimen.

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The detailed description is described with reference to the accompanying figures. In the figures, the left-most digit(s) of a reference number identifies the figure in which the reference

DETAILED DESCRIPTION

Embodiments of the present disclosure are directed to, among other things, techniques and systems for recognizing a user of a networked fitness system and initiating a customized exercise routine for the recognized user. Although the embodiments disclosed herein are often described with reference to a networked fitness machine, it is to be appreciated that other types of devices constituting the networked fitness system can be used in lieu of a fitness machine, such as mobile computing devices and/or wearable devices (e.g., smart watches, fitness bands, etc.). Furthermore, although a fitness machine in the form of a treadmill is often described in examples herein, other types of stationary exercise devices can be used with the techniques and systems disclosed herein without changing the basic characteristics of the system. Such other types of stationary exercise devices that may make up part of the fitness machine disclosed herein include, but are not limited to, elliptical machines, stationary bicycles, rowing machines, stair climbers, exercise pools (i.e., swimming machines), weight machines, and similar types of devices. Moreover, it is to be appreciated that the embodiments disclosed herein may comprise fitness machines built for cardiovascular exercise, strength exercise (e.g., weight machines), and/or flexibility exercise.

In other embodiments, the networked fitness system may include intelligent sensors communicatively coupled to a networked computing device that may be implemented in other suitable environments, such as outdoors (e.g., mobile devices like smartphones, or wearables like fitness bands, smart watches, etc.), a user's living room, or on recreational and/or fitness equipment such as bicycles, rowing boats (e.g., canoes, kayaks, etc.), or any other similar structure used for exercise and/or recreational activities.

The disclosed fitness system may be implemented and used in various environments and settings, including, but not limited to, health clubs or gyms, medical rehabilitation centers, corporate offices, household fitness environments, outdoor environments, and the like. The embodiments disclosed herein pertain to a system (such as a fitness machine) that is network-enabled to allow for cloud-based access of user profile information and fitness data in order to provide customized exercise routines for users from a networked fitness system disposed at any location. In some embodiments, user interface aspects of the system may be in the form of a virtual assistant or virtual persona that assists the user with his/her workout regimen.

The techniques and systems described herein may be implemented in a number of ways. Example implementations are provided below with reference to the following figures.

Example Environment

Figure 1:
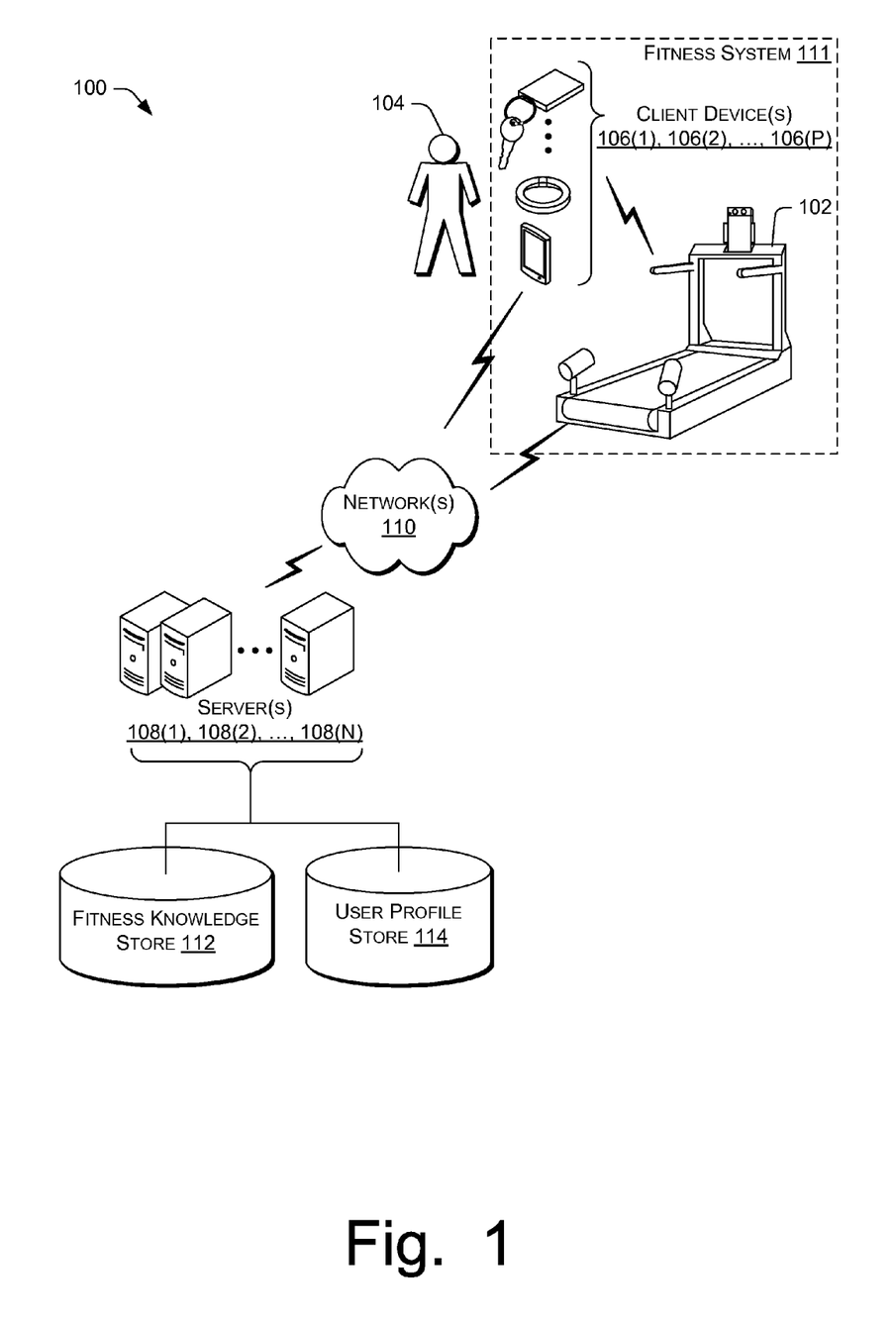
FIG. 1 illustrates an example environment of a cloud-based system (or platform) for implementing a user-customized fitness experience.

FIG. 1 illustrates an example environment of a cloud-based system 100 including, among other things, a networked fitness machine 102 (sometimes referred to herein as a "smart fitness machine 102", or simply a "fitness machine 102"). In the cloud-based system 100, a user(s) 104 is associated with the networked fitness machine 102 at any given time, such as when the user 104 decides to exercise on the networked fitness machine 102.

The user 104 may also be associated with one or more client computing devices ("client devices") 106(1), 106(2), . . . , 106(P) that are configured to communicate via wired or wireless communication with the networked fitness machine 102, and further to access, or cause the networked fitness machine 102 to access, one or more servers 108(1), 108(2), . . . , 108(N) via a network(s) 110. For example, the client device(s) 106(1)-(P) may be physically connected to the networked fitness machine 102 through electrical couplings such as wires, pins, connectors, etc., to utilize a wired communication protocol (e.g., universal serial bus (USB)), or the client device(s) 106(1)-(P) may be wirelessly connected to the networked fitness machine 102, such as via WiFi protocol, a short-wave radio frequency (e.g., Bluetooth®), or another suitable wireless communication protocol. The client device(s) 106(1)-(P) may further utilize a communication interface to access the server(s) 108(1)-(N) via the network 110. In some embodiments, the client device(s) 106(1)-(P) have their own built in transceiver (e.g., a cellular transceiver or other suitable wireless transceiver of a smart phone) to access the server(s) 108(1)-(N) over the network 110. The user 104 may represent various different types of users, such as a user 104 interested in casual fitness, recreational fitness, or a competitive or professional athlete. Such different types of users are discussed in more detail below with reference to user profiles.

In general, the client device(s) 106(1)-(P) and/or the networked fitness machine 102 may constitute a networked fitness system 111. The networked fitness system 111 (or any individual device thereof), either automatically or at the direction of the user 104, may access the server(s) 108(1)-(N) via the network 110 to obtain or upload various types of data, and the networked fitness system 111 may also receive messages such as email, short message service (SMS) text messages, messages via an application associated with client device(s) 106(1)-(P) or the networked fitness machine 102, and the like, via the network 110.

The client device(s) 106(1)-(P) may be implemented as any number of computing devices, including a personal computer, a laptop computer, a tablet computer, a portable digital assistant (PDA), a mobile (smart) phone, fitness trackers (e.g., a Nike® FuelBand®, FitBit® activity trackers or wristbands, etc.), a thumb drive, a key fob, a portable media player, a portable game player, a smart watch, and so forth. The client device(s) 106(1)-(P) may be equipped with one or more processors and memory to store applications and data. According to some embodiments, a browser application is stored in memory of the client device(s) 106(1)-(P) and executes on the processor to provide access to the server(s) 108(1)-(N). The browser may render web pages served by a site operated by the server(s) 108(1)-(N) on an associated display of the client device(s) 106(1)-(P). The networked fitness machine 102 includes its own processor(s) and memory to enable access to the server(s) 108(1)-(N) in a similar fashion. Although embodiments are described in the context of a web based system, other types of client/server-based communications and associated application logic could be used in the cloud-based system 100. The network 110 is representative of many different types of networks, such as cable networks, the Internet, local area networks, mobile telephone networks, wide area networks and wireless networks, or a combination of such networks.

The server(s) 108(1)-(N) may be maintained and operated by an entity such as a service provider associated with the networked fitness machine 102. For example, a service that facilitates cloud-based storage and management of fitness data for users may maintain the server(s) 108(1)-(N) to provide various fitness services to the user 104. For example, the servers(s) 108(1)-(N) may handle requests, such as in the form of a uniform resource locator (URL), from the networked fitness machine 102 and/or the client device 106, and serve, in response, various information and data, such as in the form of a web page, to the networked fitness machine 102 and/or the client device 106, allowing the user 104 to interact with the data provided by the server(s) 108(1)-(N). In this manner, an entity maintaining the server(s) 108(1)-(N) is representative of essentially any service provider supporting user interaction with fitness-related data, including health club sites, equipment maker sites, social networking sites, etc.

In some embodiments, the server(s) 108(1)-(N) have access to a fitness knowledge store 112 that is a repository of fitness knowledge information, such as how to walk, run, stretch, bike, row, etc. with proper body form. The fitness knowledge store 112 may also contain information pertaining to preferable levels, and/or ranges, of body mass index (BMI), heart rate, hydration, blood pressure, blood glucose, respiratory rate, temperature, and the like that may be mapped across various activity levels (e.g., moderate vs. intense exercise) and/or demographic information that may include age, gender, race or ethnicity. For instance, health and fitness experts (e.g., sports medicine experts) and other resources may be utilized to populate the fitness knowledge store 112 with information on recommended exercise regimens, including frequency, intensity, and duration of workouts recommended across various user profile types. Such a fitness knowledge store 112 may be leveraged for customization of exercise routines, providing constructive feedback to specific individuals based on known information about the individuals, and so forth.

In some embodiments, the server(s) 108(1)-(N) also have access to a user profile store 114 that stores information on multiple users, including the user 104 of FIG. 1. The user profile store 114 maintains profiles for individual users based on collected information about the user. The user profiles may associate with the user information including, but not limited to, a username and password, name of the user, mailing address, phone number, electronic mail (e-mail) address, social media accounts and profiles (e.g., Facebook®, Twitter®, etc.), gender (e.g., male or female), date of birth (i.e., age), race or ethnicity, height, weight, health conditions (e.g., heart disease, cancer, previous strokes, respiratory disease, injuries, diabetes, Alzheimer's disease, depression, liver disease, kidney disease, blood pressure, etc.).

In some embodiments, various types of security credentials may be setup for the user 104 and maintained in the user profile store 114. The security credentials may include, but are not limited to, the aforementioned username and password combination, biometrics (e.g., fingerprint or facial recognition information, etc.), unique device identifiers, registered inter-net protocol (IP) addresses of client computing device(s) 106(1)-(P) used by the user 104, security questions, and other security credentials. In some embodiments, such security credentials may add a layer of security for confirmation of the identity of the user 104 upon accessing the networked fitness machine 102.

The user 104 may provide fitness goals or objectives as part of an initial profile setup to be stored in the user profile store 114. For example, categories such as "lose weight", "stay fit", "improve endurance", "train for race", or "recover from injury (rehabilitation)" are examples of options that may be provided to a user 104 for selection of a fitness goal. In some embodiments, specific events (e.g., the Boston Marathon) may be specified by the user 104 as a specific goal for training purposes. In this scenario, the networked fitness machine 102 may be configured to present a virtual course of the specific event during the exercise routine so that the user 104 can simulate the event for training purposes.

In some embodiments, the user 104 may access a site on the server(s) 108(1)-(N) to answer a questionnaire that facilitates automated selection, by the server(s) 108(1)-(N), of a fitness goal. In some embodiments, the user profile store 114 further maintains schedule information for the user 104, such as a schedule that indicates dates and times of upcoming exercise routines according to a prescribed exercise regimen. This schedule may consider an availability of the user 104 based on a personal calendar of the user 104. As such, an exercise regimen may be catered to a user 104 depending on his/her availability. For example, a full-time worker may only have an hour or two each day available for exercise, while a professional athlete who is devoted to training full time may be available to exercise much more frequently (e.g., multiple times throughout a single day and for extended duration).

In some embodiments, users that setup profiles in the user profile store 114 may be categorized according to profile types. This categorization may be based on explicit selection by the user 104, or alternatively, the server(s) 108(1)-(N) may be configured to determine a categorization for users based on information provided by the users, or based on answers to predetermined questions. An illustrative example of possible categories for profile types are: (1) Casual Fitness; (2) Recreational; (3) Competitive; and (4) Physical Therapy. Attributes of the "Casual Fitness" profile type may be users that: would like to lose weight or get in shape, are not serious about running, may be fine with just walking for exercise, are not consistent with an exercise regimen, are unsure about technology, may have medical issues, are not receptive to online training, and are not motivated to train or adjust. Attributes of the "Recreational" profile type may be users that: are casual runners, may be interested in running, may be interested in exercising, are fairly regular with an exercise regimen, are receptive to technology, exercise to aid medical issues, utilize online training, and are easier to train and adjust. Attributes of the "Competitive" profile type may be users that: are active runners, enjoy running, are excited about competing, are consistent in a daily exercise regimen, are very selective in technology, have minimal health issues, seek professional training, and are harder to teach. Attributes of the "Physical Therapy" profile type may be users that: have suffered a physical injury and are using exercise as physical therapy in an effort to rehabilitate and get healthy.

At least some of the information maintained in the user profile store 114 may be received from explicit user input via a user interface of either or both of the client device(s) 106(1)-(P) or the networked fitness machine 102, while some of the information may include implicit information received via sensors of the networked fitness machine 102 (e.g., heart rate, weight for BMI calculation, body temperature, etc.), or from other sources, such as other fitness related products that track workout history information (e.g., Nike® FuelBand, FitBit® trackers and wristbands, etc.). With more information obtained from the user 104, a more complete a user profile may be created and stored in the user profile store 114 for use by the networked fitness machine 102.

Example Client Device-Fitness Machine Coupling

Figure 2:
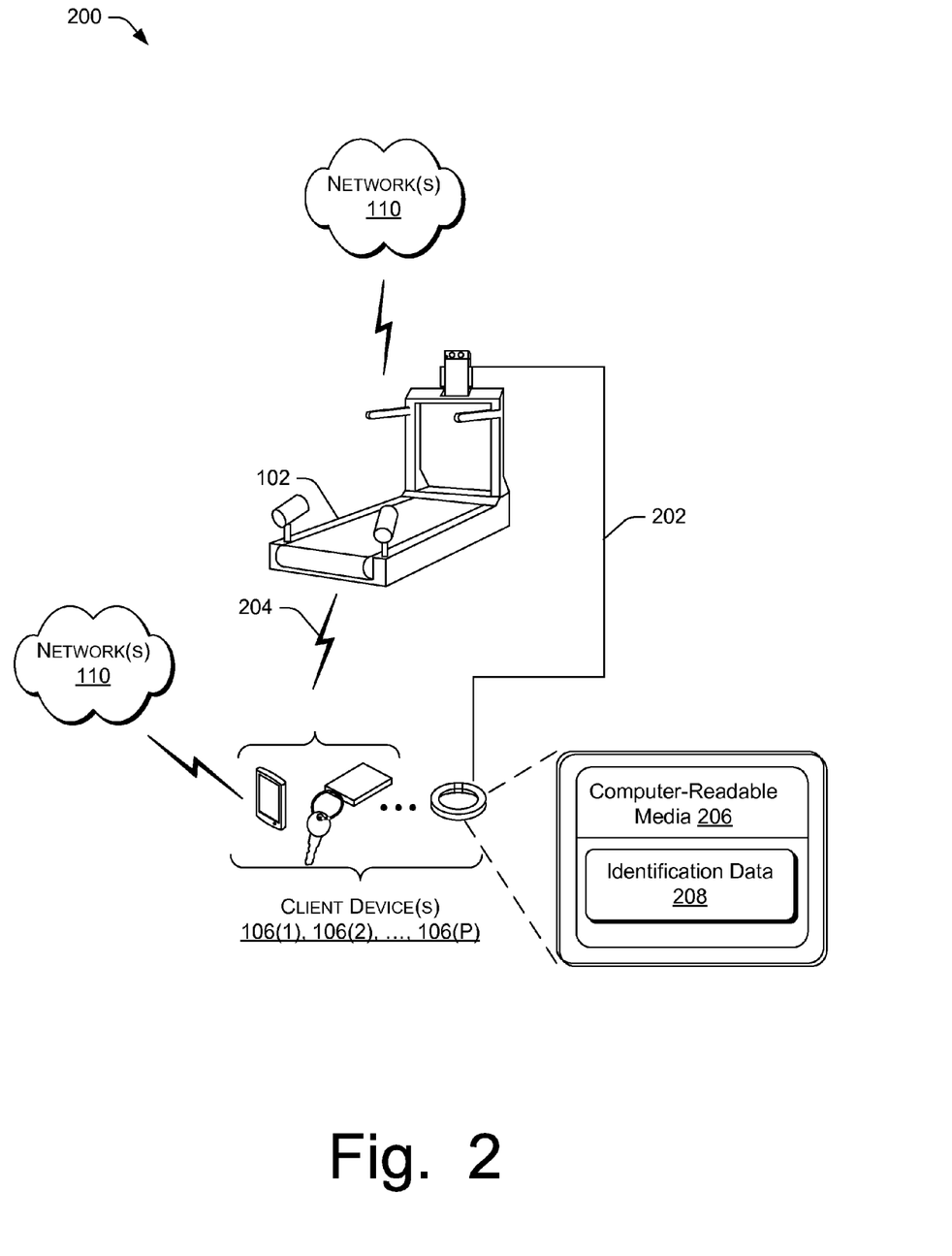
FIG. 2 illustrates an example sub-environment of the cloud-based system (or platform) of FIG. 1 illustrating communicative coupling between a client device(s) and the networked fitness machine.

FIG. 2 illustrates an example sub-environment 200 of the cloud-based system 100 of FIG. 1 illustrating communicative coupling between the client device(s) 106(1)-(P) and the networked fitness machine 102. As mentioned above, the client device(s) 106(1)-(P) may be implemented as any number of computing devices, such as those described above with reference to FIG. 1. Examples of the client device(s) 106(1)-(P) are shown in FIGS. 1 and 2 as being a smart phone, a key fob, and a fitness tracker (i.e., activity tracking (fitness) wristband), among other possible devices that may be suitable for the client device(s) 106(1)-(P). The client device(s) 106(1)-(P) may be physically connected to the networked fitness machine 102 through electrical coupling 202, including, but not limited to, wires, pins, connectors, cables, and the like. For example, a client device 106 may be connected via the electrical coupling 202 in the form of a USB connector, or similar connector, provided on the networked fitness machine 102. In some embodiments, the client device(s) 106 and the fitness machine 102 may represent the networked fitness system 111 introduced in FIG. 1. In other embodiments, either the fitness machine 102 or the client device(s) 106 may individually represent the networked fitness system 111.

In some embodiments, the client device(s) 106(1)-(P) may be connected to the networked fitness machine 102 via a wireless coupling 204, such as via WiFi protocol, a shortwave radio frequency (e.g., Bluetooth®), or another suitable wireless communication protocol. In some embodiments, infrared (IR) data transmission may be utilized to wirelessly communicate between the client device(s) 106(1)-(P) and the networked fitness machine 102. As depicted in FIG. 2, at least some of the client device(s) 106(1)-(P) may be configured to communicate with other remote computing devices (e.g., the server(s) 108(1)-(N)) using a communication interface of the client device(s) 106(1)-(P). For example, a client device 106 in the form of a smart phone may be capable of accessing the server(s) 108(1)-(N) via the network(s) 110.

FIG. 2 also illustrates that client device(s) 106(1)-(P) may comprise computer-readable memory 206 storing identification data 208 therein. The identification data 208 may be associated with the user 104 in the user profile store 114 of FIG. 1. For example, a user 104 may associate a unique device identifier (e.g., an IP address of a smart phone, an alphanumeric code, etc.) of the client device(s) 106(1)-(P) with his/her profile. It is to be appreciated that the identification data 208 may comprise any suitable type of data that uniquely identifies the user 104 or the client device(s) 106(1)-(P) that may be owned by the user 104. In one illustrative example, the user 104, upon registering with a fitness service that maintains the server(s) 108(1)-(N), may provide the server(s) 108(1)-(N) with the identification data 208 for association with his/her user profile, such as by plugging the client device(s) 106(1)-(P) into a personal computer, operating a soft or hard button on the client device(s) 106(1)-(P), manual user input, or any suitable technique for associating the client device(s) 106(1)-(P) with the user 104 via the user's profile. The identification data 208 enables any networked fitness machine 102 and/or the server(s) 108(1)-(N) to recognize the user 104 when the user 104 accesses the networked fitness machine 102, even if the user 104 has never before used a particular networked fitness machine 102.

It is to be appreciated that identification data 208, as disclosed herein, is not limited to "device-specific" identification data 208. That is, other types of identification data 208 may identify the user 104. Such identification data 208 may include, but is not limited to, biometric information that may be received by the networked fitness machine 102, such as image data of the user's face, fingerprint information, and the like.

Example Networked Fitness System

Figure 3:
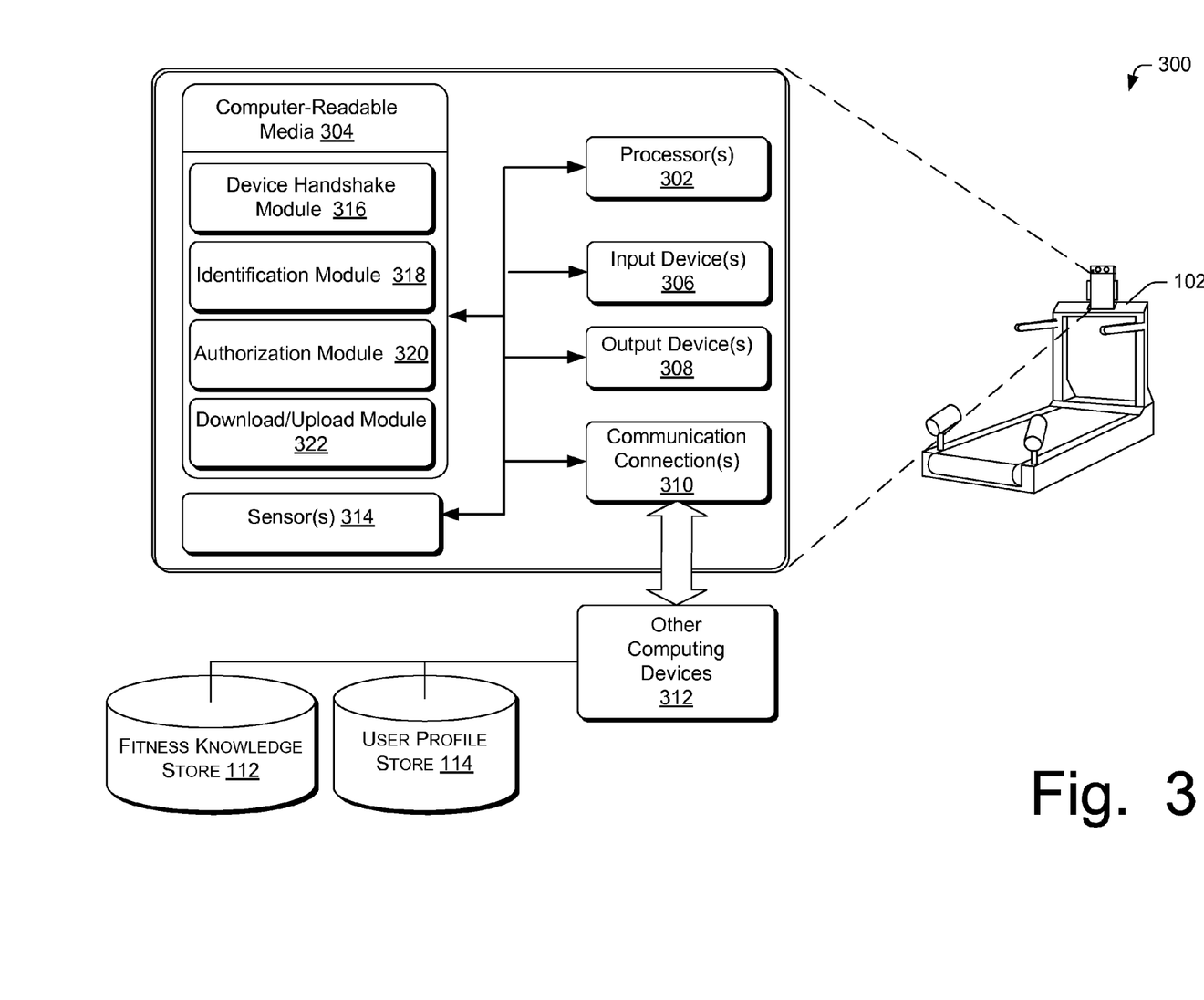
FIG. 3 is a block diagram of an example computing environment of an example fitness machine, including various components of the fitness machine.

FIG. 3 is a block diagram of an example computing environment 300 including an example networked fitness system 111, such as the networked fitness machine 102 of FIG. 1. The computing environment 300 shown in FIG. 3 is only one illustrative example of a computing environment and is not intended to suggest any limitation as to the scope of use or functionality of the computing environment 300. Neither should the computing environment 300 be interpreted as having any dependency nor requirement relating to any one or combination of components illustrated in FIG. 3.

In at least one configuration, the networked fitness machine 102 comprises one or more processors 302 and computer-readable media 304. The networked fitness machine 102 may also include additional data storage devices (removable and/or non-removable) such as, for example, magnetic disks, optical disks, or tape. Such additional storage may include removable storage and/or non-removable storage. Computer-readable media 304 may include, at least, two types of computer-readable media 304, namely computer storage media and communication media. Computer storage media may include volatile and non-volatile, removable, and non-removable media implemented in any method or technology for storage of information, such as computer readable instructions, data structures, program modules, or other data. The system memory, the removable storage and the non-removable storage are all examples of computer storage media. Computer storage media includes, but is not limited to, random access memory (RAM), read-only memory (ROM), erasable programmable read-only memory (EEPROM), flash memory or other memory technology, compact disc read-only memory (CD-ROM), digital versatile disks (DVD), or other optical storage, magnetic cassettes, magnetic tape, magnetic disk storage or other magnetic storage devices, or any other non-transmission medium that may be used to store the desired information and which may be accessed by the networked fitness machine 102. Any such computer storage media may be part of the networked fitness machine 102. Moreover, the computer-readable media 304 may include computer-executable instructions that, when executed by the processor(s) 302, perform various functions and/or operations described herein.

In contrast, communication media may embody computer-readable instructions, data structures, program modules, or other data in a modulated data signal, such as a carrier wave, or other transmission mechanism. As defined herein, computer storage media does not include communication media.

The networked fitness machine 102 may include one or more input devices 306, such as a touch screen (e.g., touch, or proximity-based) display, physical buttons (e.g., keyboard or keypad) on the networked fitness machine 102, a camera-based sensor configured to receive gestural input from the user 104, a microphone or microphone array for receiving voice input commands from the user 104, pointing devices (e.g., mouse, pen, stylus, etc.), remote controls, or any other suitable input device for interfacing with the networked fitness machine 102.

The networked fitness machine 102 may include one or more output devices 308 such as a display (e.g., liquid crystal display (LCD)), one or more speakers, or any other suitable output device coupled communicatively to the processor(s) 302 and the computer-readable media 304. The output devices 308 may serve the purpose of providing output to the user 104, such as providing fitness related information via a display, for example, providing an evaluation of the user's exercise performance and/or an instruction for the user 104 to take corrective action during an exercise routine, music, video, virtual courses, and so forth. The networked fitness machine 102 may be configured to provide any suitable visual data via a display to the user, such as cable television content, streamed video, image or text data, such as from the server(s) 108(1)-(N). The display 206 may further be configured to enter a "sleep" state after a predetermined time has passed with no input to the networked fitness machine 102.

The networked fitness machine 102 may further contain communications connection(s) 310 that allow the networked fitness machine 102 to communicate with other computing devices 312 such as via a network. The other computing devices 312 may include the client devices 106(1)-(P) and the server(s) 108(1)-(N), among other computing devices 312. Accordingly, the communications connection(s) 310 may facilitate communication over the network(s) 110 to enable the networked fitness machine 102 to access the fitness knowledge store 112 and/or the user profile store 114. Additionally, the communications connection(s) 310 may enable WiFi-based communication such as via frequencies defined by the IEEE 802.11 standards, short range wireless frequencies such as Bluetooth®, or any suitable wired or wireless communications protocol that enables the networked fitness machine 102 to interface with the other computing devices 312 in relatively close proximity to the networked fitness machine 102.

The networked fitness machine 102 may further include one or more sensors 314 communicatively coupled (wired and/or wireless) to the networked fitness machine 102. The sensor(s) 314 may be communicatively coupled to the networked fitness machine 102 via wired or wireless (e.g., Bluetooth®) connection in order to transmit collected information about the user 104 to the networked fitness machine 102 where it may be analyzed and interpreted for various applications. In some embodiments, the sensor(s) 314 include one or more camera-based sensors mounted at any suitable location on the networked fitness machine 102 (e.g., a front end of the networked fitness machine 102) and configured to detect image data of the user 104 on the networked fitness machine 102. A camera-based sensor may comprise a capture device in the form of a depth camera configured to visually monitor the user 104 by collecting image data of the user 104. One suitable example device that may be used as a camera-based sensor is the Kinect® sensor used with the Xbox® console system from Microsoft® Corporation of Redmond, Wash. Such a camera-based sensor may be configured to continuously detect image data (i.e., capture video) of the user 104 with depth information so that movements of the user 104 may be interpreted by onboard processing units of the camera-based sensor 204 and/or computing components of the networked fitness machine 102. The camera-based sensor 204 may use any suitable technique to capture image data with depth information (e.g., time-of-flight (ToF), structured light imaging, stereo imaging, etc.) to facilitate the techniques described herein.

In some embodiments, a camera-based sensor used as the sensor 314 may track movements of the user 104 during an exercise routine, receive gestural input commands from the user 104, identify the user 104 with face recognition techniques, and other similar functions. For example, the server(s) 108(1)-(N) may collect image data of the faces of registered or subscribed users of the cloud-based system 100 of FIG. 1 upon, or after, initial registration with a fitness information service. Accordingly, upon the user 104 positioning himself/herself in front of a camera-based sensor of the networked fitness machine 102, such as at the beginning of an exercise routine, the networked fitness machine 102 may recognize the user 104 by identifying the face of the user 104. In some embodiments, the camera-based sensor 204 may be configured to detect a heart rate of the user 104 by detecting changes in skin tone or with other suitable visual cues, facial expressions to interpret emotional states (e.g., happy, worried, sad, etc.) of the user 104, muscle tension of the user 104 for various muscle groups (e.g., neck, shoulders, hands, etc.) based on suitable visual cues, such as by a flex angle of limbs.

In some embodiments, one or more additional cameras may be disposed on the fitness machine 102 to collect image data from different vantage points. For example, vantage points from a back end of the fitness machine 102 may enable additional cameras placed in those locations to detect a substantial portion, if not all, of the user's profile. The additional cameras may also be depth cameras that utilize, for example, infrared (IR) camera-based technology. In some embodiments, the additional cameras are configured to detect image data of the user 104, which may be processed by downstream components of the fitness machine 102 by utilizing image stitching software to compose a three-dimensional (3D) model of the user 104 based on separate two-dimensional (2D) images obtained from each of the additional cameras.

In some embodiments, the one or more sensors 314 may further include one or more user information sensors, such as a substantially noninvasive scanning device. The sensor(s) 314 may be substantially noninvasive in that they do not require blood samples, urine, or anything that may substantially interrupt the user 104 during an exercise routine. In fact, the one or more sensors 314 may not need any user intervention to detect vital information (e.g., using optical-based detection). In some embodiments, the one or more sensors may be operated by the user 104 contacting his/her forehead with a scanning device in order to measure vital information. This substantially noninvasive technique for taking vital measurements is suitable for use on the networked fitness machine 102, leaving the user 104 substantially uninterrupted during an exercise routine.

In some embodiments, the sensor(s) 314 may be included as part of a wearable device, such as a smart watch or fitness band to be worn by the user 104, and may be utilized for a substantially noninvasive scanning device. In some cases, a medical tricorder may be utilized to take health measurements (vital information) including, but not limited to, heart rate, blood pressure, body temperature, oximetry (blood oxygenation), hydration, heart rate variability (HRV), pulse wave transit time (PWTT) (i.e., a measure of the time it takes for a beat from the user's heart to reach somewhere else in the user's body), and the like. A scanning device may be further configured to run an electrocardiogram (EKG), detect stress levels, and so forth.

In some embodiments, the sensor(s) 314 include sensors configured to obtain respiratory rate, blood glucose (e.g., by taking sweat samples of the user 104), and the like. In some embodiments, the networked fitness machine 102 may be further configured to receive and process data from external sensors that are provided by the user 104, such as electronic textile (e-textile) sensors embedded in a garment of the user 104, such as a sock, shirt, hat, and the like to detect health or performance-based measurements (e.g., pressure distribution on the foot of the user 104).

Together, the sensors 314 are configured to collect various types of information about the user 104. For instance, one or more camera-based sensors may collect image data from the user 104 before, during, and after exercising on the networked fitness machine 102. Other ones of the sensors 314 may be configured to collect other types of information about the user 104, such as vital measurements, and similar information that may not be detectable from visual cues alone.

The computer-readable media 304 of the networked fitness machine 102 may store various modules, including a device handshake module 316, an identification module 318, an authorization module 320, and a download/upload module 322. The device handshake module 316 may facilitate a handshake operation between the networked fitness machine 102 and a device in close proximity to it, such as the client device(s) 106(1)-(P) when it is brought close to, or connected to, the networked fitness machine 102 by the user 104. For example, the client device(s) 106(1)-(P), upon connection, or bringing the client device(s) 106(1)-(P) in close proximity to the networked fitness machine 102, may transmit, via wired or wireless communication, the identification data 208 to the networked fitness machine 102 to identify the client device(s) 106(1)-(P) and to enable communication between the client device(s) 106(1)-(P) and the networked fitness machine 102. One example scenario of when the handshake module 316 may be used is when the user 104 desires to stream music from the client device(s) 106(1)-(P) to the networked fitness machine 102 for playback via the speakers of the networked fitness machine 102. Other data transfer applications may be enabled by a handshaking operation without changing the basic characteristics of the system.

The identification module 318 may be configured to receive the identification data 208 (e.g., device identifier, biometrics, etc.) that is associated with the user 104, and to cause transmission of the received identification data 208 via the communication connection(s) 310 to the server(s) 108(1)-(N). The server(s) 108(1)-(N) may utilize this identification data 208 to locate a user identification (1D) (e.g., username, personal identification number (PIN), and the like) of the user 104 so that the networked fitness machine 102 may initiate a customized exercise routine for the user 104.

The authorization module 320 may be configured to receive the user ID from the server(s) 108(1)-(N) in response to the transmission of the identification data 208. In some embodiments, the authorization module 320 may further request and receive confirmation from the user 104 that the user ID corresponds to the user 104. This confirmation may act as an added layer of security to ensure that the user 104 is properly identified. The confirmation received by the authorization module 320 may simply be a "yes" or "no" indication received from the user via the input device(s) 306 of the networked fitness machine 102, and/or it may involve receiving security credentials from the user 104 (e.g., a password, an answer to a security question, etc.).

The download/upload module 322 may be configured to automatically download, in response to receiving the confirmation from the user 104, a customized exercise routine associated with the user 104 from the server(s) 108(1)-(N). In some embodiments, the customized exercise routine may have been prescribed and scheduled previously by a program running on the server(s) 108(1)-(N). In other embodiments, the customized exercise routine may be a modification of a prescribed exercise routine obtained from the server(s) 108(1)-(N), the modification determined according to current subjective feedback received from the user 104 and/or currently sensed vital information about the user 104. For example, if the user 104 specifies, via the input device(s) 306 of the networked fitness machine 102 that he/she is feeling sick at the time of using the networked fitness machine 102, a prescribed exercise routine obtained from the server(s) 108(1)-(N) may be modified by the fitness machine 102 that aims to reduce the intensity of the routine due to the illness felt by the user 104. As another example, the sensor(s) 314 may detect an abnormally high heart rate of the user 104, and may modify a prescribed workout accordingly.

The download/upload module 322 may be further configured to upload a workout summary after completion or termination of the customized exercise routine. For example, information obtained during the workout from the sensors 314 (e.g., image data, vital information, performance information, etc.) may be uploaded to the server(s) 108(1)-(N) for inclusion in a workout summary. Other subjective feedback information may be obtained from the user 104 before, during, or after the exercise routine that may also be uploaded to the server(s) 108(1)-(N) by the download/upload module 322 for storage in the user profile store 114. Accordingly, an ongoing workout history and user profile may be built to track performance, show trends, make recommendations and instructions for improvement, etc.

In some embodiments, the networked fitness machine 102 is configured to generate and display, via the output device(s) 308 (e.g., a display), an avatar of the user 104 based on information about the user 104 in the user profile store 114 and/or data collected from the sensor(s) 314. The avatar provided by the networked fitness machine 102 may be any graphical representation of the user 104 in two-dimensional or three-dimensional form. In some embodiments, the avatar may loosely resemble the physical appearance of the user 104 and track the user's progress by changing the appearance of the avatar as the user loses (or gains) weight and/or gains (or loses) strength. For example, based on height, weight, gender, and other suitable information obtained about the user 104 from the user 104 and/or the sensors 314, an avatar may be created that is reflective of the user's traits and state of fitness that may be visually depicted by the avatar. The networked fitness machine 102 may be configured to present current avatars with (e.g., next to) previous avatars of the user 104 that were generated days, weeks, months, or years earlier in order to show progress that the user 104 has made over time in terms of his/her fitness. In some embodiments, the user 104 may customize or otherwise manipulate the avatar. For example, the user 104 may select different hair colors, hair styles, clothing, body markings or piercings, and the like, to be shown on the avatar. The networked fitness machine 102 may further be configured to enable other entertainment-related functions, such as to output a competitor avatar to virtually compete with the user 104 during the exercise routine, scenery (e.g., varying landscapes that change with movement of the user 104 while on the networked fitness machine 102, specific race courses, etc.), music, and/or video media.

It is to be appreciated that some or all of the components and corresponding functionality described herein with reference to FIG. 3 may be provided by one or more of the client devices 106(1)-(P) that may represent the networked fitness system 111. For example, an application on a mobile phone and/or a wearable computer (e.g., a smart watch) may be used to download a customized exercise routine associated with a user 104 of the client device(s) 106(1)-(P) so that the user 104 can perform the customized exercise routine in any suitable environment, such as outdoors. In another example, the sensors 314 may be mounted at any suitable location (e.g., in a living room of a user's home) and coupled to (e.g., embedded within) a networked client device 106 so that the sensors 314 can collect fitness-related information about the user 104, even when the user 104 is not on a fitness machine 102. In these scenarios, the sensors 314 may be capable of being mounted on a variety of structures in different environments (e.g., flat surface mounting, clips, ball-and-socket mounts, etc.), or otherwise be embedded in a client device 106 that may be carried or worn by the user 104. The more sensors 314 that are available to collect information may allow for more accurate customization of exercise regimens. For example, a fitness machine 102 equipped with a high number of sensors 314 may more accurately assess fitness-related information about the user 104 than a wearable device 106 with fewer available sensors 314.

Example Server(s)

Figure 4:
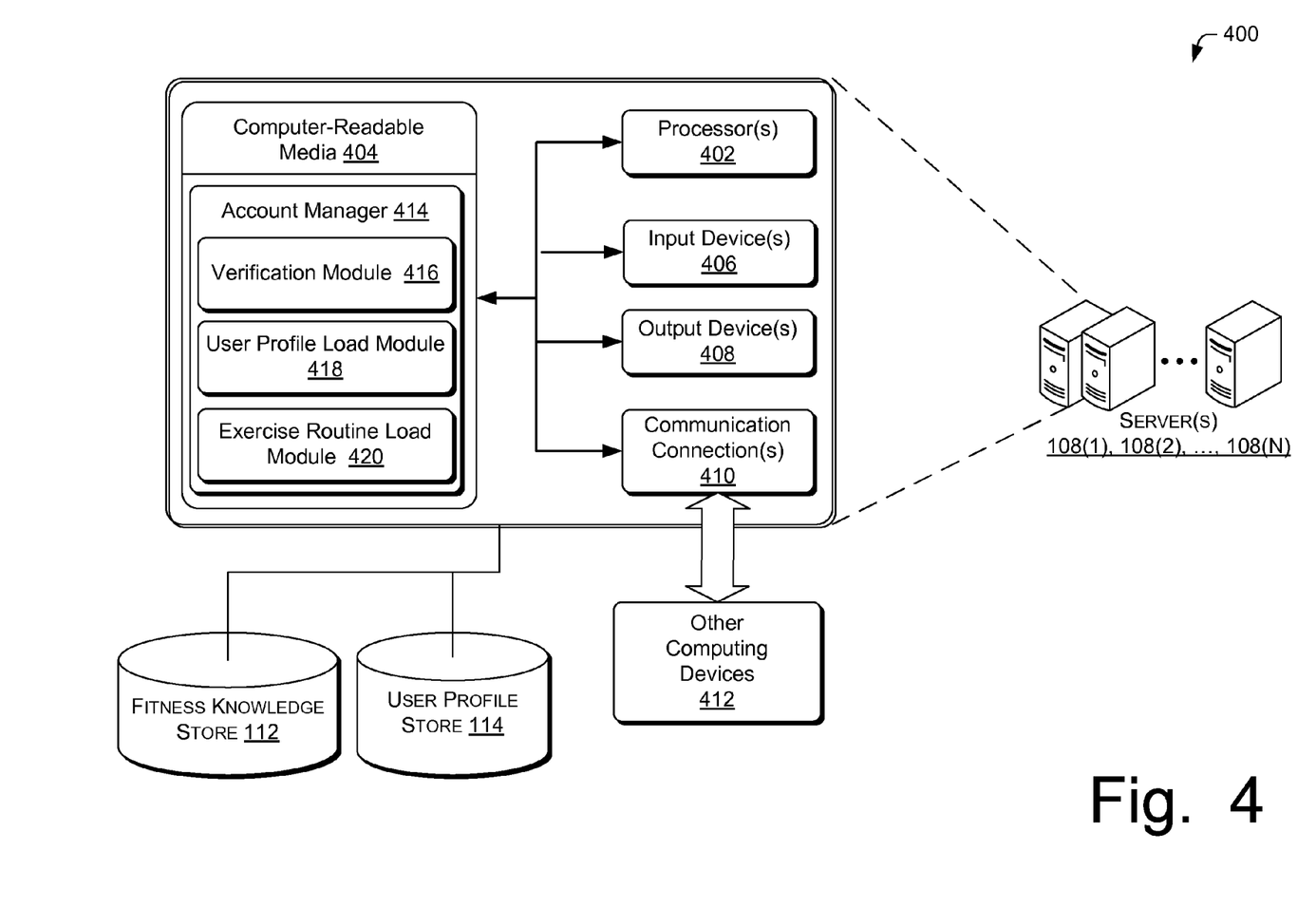
FIG. 4 is a block diagram of a computing environment including an example server(s), including various components of the server(s).

FIG. 4 is a block diagram of a computing environment 400 including example server(s) 108(1)-(N), including various components of the server(s) 108(1)-(N). The computing environment 400 shown in FIG. 4 is only one illustrative example of a computing environment and is not intended to suggest any limitation as to the scope of use or functionality of the computing environment 400. Neither should the computing environment 400 be interpreted as having any dependency nor requirement relating to any one or combination of components illustrated in FIG. 4.

In at least one configuration, the server(s) 108(1)-(N) comprises one or more processors 402 and computer-readable media 404. The server(s) 108(1)-(N) may also include additional data storage devices (removable and/or non-removable) such as, for example, magnetic disks, optical disks, or tape. Such additional storage may include removable storage and/or non-removable storage. Computer-readable media 404 may include, at least, two types of computer-readable media 404, namely computer storage media and communication media, as described above with reference to the computer-readable media 304 of FIG. 3.

The server(s) 108(1)-(N) may include one or more input devices 406, such as keyboards, pointing devices (e.g., mouse, pen, stylus, etc.), or any other suitable input device for interfacing with the server(s) 108(1)-(N). The server(s) 108 (1)-(N) may also include one or more output devices 408 such as a display, speakers, or any other suitable output device coupled communicatively to the processor(s) 402 and the computer-readable media 404.

The server(s) 108(1)-(N) may further contain communications connection(s) 410 that allow the server(s) 108(1)-(N) to communicate with other computing devices 412 such as via a network. The other computing devices 412 may include the client device(s) 106(1)-(P) and the networked fitness system (e.g., the networked fitness machine 102), among other computing devices 412. Accordingly, the communications connection(s) 410 may facilitate communication over the network(s) 110 to enable the networked fitness machine 102 and/or the client device(s) 106(1)-(P) to access the fitness knowledge store 112 and/or the user profile store 114.

The computer-readable media 404 of the server(s) 108(1)-(N) may store various modules, including an account manager 414 to manage user profile information of the users maintained in the user profile store 114. The account manager 414 may include a verification module 416, a user profile load module 418, and an exercise routine load module 420. The verification module 416 may be configured to receive the identification data 208 from the networked fitness machine 102, locate or lookup a user ID corresponding to the identification data 208 within the user profile store 114, and transmit the user ID to the networked fitness machine 102. In some embodiments, the verification module 416 is configured to transmit security credentials associated with the user ID to the networked fitness machine 102 for verification of the user's identity. For example, a security question may be transmitted with the user ID that the user 104 is to answer in order to download and initiate a customized exercise routine for the user associated with the user ID.

The user profile load module 418 may be configured to download, upon a request from the networked fitness machine 102, information about the user 104 obtained from a user profile stored in the user profile store 114. For example, height, gender, or other suitable information previously collected from the user 104 may be loaded onto the networked fitness machine 102 by the user profile load module 418. Other information, such as previously created avatars of the user, fitness-related goals of the user, and the like, may be transmitted to the networked fitness machine 102 by the user profile load module 418.

The exercise routine load module 420 may be configured to transmit, in response to a request from the networked fitness machine 102, a customized exercise routine that is associated with the user ID previously located by the verification module 416. The customized exercise routine may have been previously prescribed and schedule, and may be modifiable by the networked fitness machine 102 based on sensed vital information and/or subjective feedback received from the user 104 at the networked fitness machine 102.

The exercise routine load module 420 may be further configured to receive a workout summary from the networked fitness machine 102 after completion or termination of the exercise routine. For example, information obtained during the workout from the sensors 314 (e.g., image data, vital information, performance information, etc.) may be uploaded to the server(s) 108(1)-(N) and received by the exercise routine load module 420 for inclusion in a workout summary.

In some embodiments, the account manager 414 and its subcomponents may be ultimately presented to a user 104 via the networked fitness system 111 as a virtual assistant, such as an operating system agent, that is given a persona (e.g., Zsolutionz™ Optimal Fitness Interactive Experience (ZOFIE™)) so that the user 104 may experience a more personalized or human type of interaction with the platform. Some aspects of the virtual assistant may be downloaded to the client device(s) 106 and/or the fitness machine 102 for access thereon even when a network connection is unavailable. However, information accessible to the virtual assistant may remain "in the cloud" so that the virtual assistant may provide a customized exercise experience to the user 104 from any location where a network connection is available.

Example User Setup and Exercise Routine

Use of the networked fitness machine 102 according to the embodiments disclosed herein may begin by initially creating a user profile for the user 104 that may be associated with information about the user 104 and stored in the user profile store 114. The user 104 may use any suitable computing device, such as the client device(s) 106(1)-(P) and/or the networked fitness machine 102, to input information for profile creation. Such information, as mentioned above, may include a username, password, name, mailing address, phone number, e-mail address, gender, date of birth, race or ethnicity, height, weight, health conditions (e.g., heart disease, cancer, previous strokes, etc.). The user 104 may link other accounts, such as social networking accounts as part of the setup of his/her user profile in the user profile store 114. The user 104 may provide answers to questionnaires via the client device(s) 106(1)-(P) and/or the networked fitness machine 102. The client device(s) 106(1)-(P) and/or the networked fitness machine 102 may be configured to obtain information about the user from other sources, such as a Nike® FuelBand or similar source of fitness related information.

The user 104 may input, via the client device(s) 106(1)-(P) (e.g., an application or browser) or the networked fitness machine 102 user interface, initial fitness goals, such as to "lose weight", "stay fit", "improve endurance", "train for a race," and/or "recover from injury" so that the networked fitness machine 102 may prescribe a workout regimen tailored to the user 104. The networked fitness machine 102 may deduce initial fitness goals based on answers to specific questions provided to the user 104. The user 104 may further specify a current physical health level, diet or daily calorie intake, availability, activity level (casual vs. competitive), workout history, and any pertinent exercise routines that the user 104 may prefer over others.

Once all of the relevant information is collected from the user 104 and a profile is created, the networked fitness machine 102 and/or the client device 106 may display options of how long a particular workout regimen will take with and without dieting. The user 104 may select an option based on whether he/she desires to change their diet according to the diets specified by the networked fitness machine 102. Other useful links may be provided to the user 104 to augment the prescribed workout regimen, such as other forms of cross training, weight training, resistance training, and the like.

The following paragraphs describe a plurality of "phases" for a workout program. Any individual phase may be optional, and thereby omitted from the overall set of phases that are implemented. In this sense, some or all of the following phases may be implemented as part of the exercise regimen for a user 104.

Phase I

When the user 104 approaches a networked fitness machine, such as the networked fitness machine 102, the networked fitness machine 102 receives identification data 208 associated with the user 104. As described above, the identification data 208 may be received from the client device(s) 106(1)-(P). In some embodiments, the identification data 208 may comprise other suitable identification data 208, such as image data of the user's face used for facial recognition, or other biometrics, and so forth.

The networked fitness machine 102 may transmit the received identification data 208 to the server(s) 108(1)-(N) in order to receive a user ID from the server(s) 108(1)-(N) that corresponds to the identification data 208. The user ID may be a username of the user 104, or another suitable identifier of the user 104. The user 104 may be asked to confirm that the user ID is correct, such as by providing security credentials to verify the user's identity, and the networked fitness machine 102 may then automatically download a customized exercise routine and any other suitable user information from the server(s) 108.

Upon the user's first workout routine of a prescribed exercise regimen, a short introduction video may be presented via a display on the networked fitness machine 102 to show what will take place over the course of the prescribed exercise regimen until a goal is achieved. This could be shown each time the user 104 uses the networked fitness machine 102 and may be skipped by the user 104 after an initial viewing.

The networked fitness machine 102 may collect, via the sensors 314, current information about the user 104, including current vital measurements. For example, the sensors 314 may collect information including, but not limited to, weight (to calculate BMI with previously input height), resting heart rate, blood pressure, temperature, hydration, resting respiratory rate, blood glucose level, and other suitable health measurements.

Figure 5:
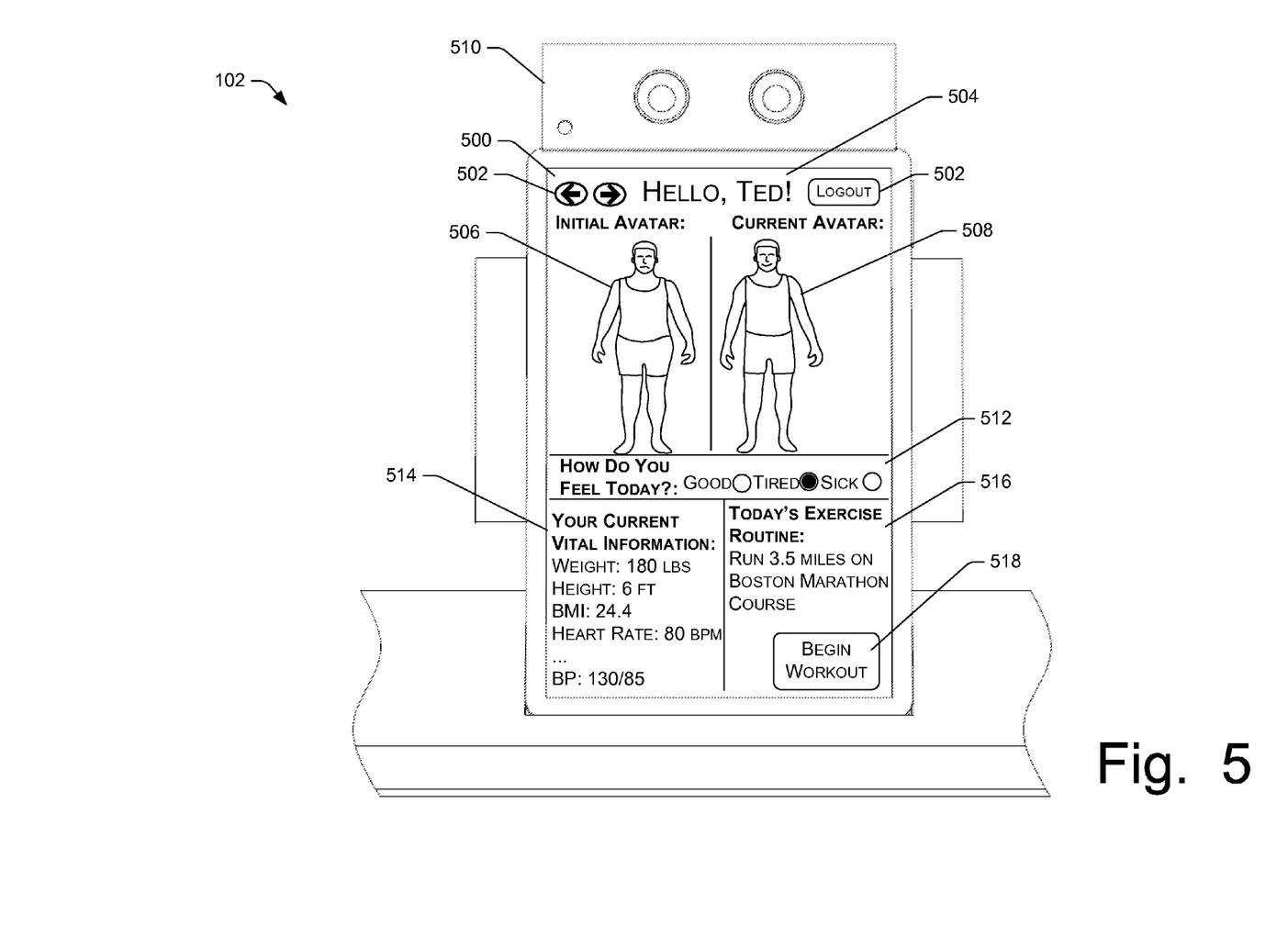
FIG. 5 illustrates a partial view of an example networked fitness machine and a user interface (UI) from the perspective of a user on the networked fitness machine, the UI providing information about the user upon start up of the networked fitness machine.

FIG. 5 illustrates a partial view of an example networked fitness machine 102 and a user interface (UI) 500 from the perspective of a user on the networked fitness machine 102. The UI 500 may be presented on a display of the networked fitness machine 102, and may provide basic navigation elements 502 (e.g., page forward, page back, logout, etc.) on the UI 500. The UI 500 may further present a welcome indication 504 (e.g., "Hello, Ted!") after the user 104 confirms his/her identity based on the user ID, as mentioned previously.

In some embodiments, various types of information about the user 104 may be downloaded by the download/upload module 322 and provided on the UI 500 of the networked-fitness machine 102, such as a previous avatar 506 that was generated at some point in the past (i.e., days, weeks, months, years, etc.) when the user 104 was in a particular state of fitness. In some embodiments, the previous avatar 506 represents an initial avatar that was generated based on information about the user 104 when the user 104 first started a prescribed exercise regimen. The previous avatar 506 may visually indicate the state of health (i.e., weight, muscle tone, etc.) of the user 104 at a time in the past. Such information may be stored in the user profile store 114.

The UI 500 may further present a current avatar 508 of the user 104 that represents a current state of health of the user 104 based on sensed measurements and/or explicit input received from the user 104. For example, a camera-based sensor 510, may capture image data of the user 104 that may be interpreted and used to render the current avatar 508 of the user 104. The networked fitness machine 102 may further account for other health or vital measurements, such as weight (to calculate BMI from height information in the user profile store 114), and other sensed information obtained by the sensors 314 of the networked fitness machine 102. The current avatar 508 may be compared to the previous avatar 506 in order to show the user 104 any progress he/she has made.

In some embodiments, the UI 500 may present a subjective feedback survey 512 comprising one or more questions regarding a current state of health, current activities that the user 104 has engaged in, or how much time the user has available for exercise. For example, the survey 512 may ask the user "How do you feel today?," with answer options of "Good," "Tired," and/or "Sick," and the like. The user 104 may select one or more of the options to provide an answer to the survey 512. Other questions may ask the user 104 how he/she slept last night, when his/her last meal was and whether it was a good meal, how his/her overall fitness is, how much time he/she has to exercise, and so forth. The survey 512 may ask the user 104 if he/she has any areas of discomfort, and the user 104 may touch the current avatar 508 at locations on the body where they are feeling discomfort to respond. In some embodiments, the subjective answers to the survey 512 may be factored into a modification of a prescribed exercise routine. For example, if a prescribed exercise routine had the user 104 running five or more miles for a single exercise routine, and the user 104 provides feedback via the survey 512 indicating that he/she is feeling sick or tired, the prescribed exercise routine may be modified to reduce the distance the user 104 is to run. The prescribed workout regimen may, in turn, be modified to compensate for such modifications (e.g., make up days and/or increased intensity or duration of future routines).

In some embodiments, the UI 500 may provide vital information 514 (or health measurements) that is obtained from the sensors 314 of the networked fitness machine 102 and/or the user profile store 114. For example, weight may be obtained from a weight sensor included as one of the sensors 314, height may be obtained from the user profile store 114, heart rate, blood pressure, and the like, may be measured by one or more of the sensors 314. Other vital measurements may be sensed and displayed via the UI 500 besides those shown in FIG. 5.

The UI 500 may further present a customized exercise routine 516 that was automatically downloaded by the download/upload module 322 upon request from the networked fitness machine 102, such as after receipt of a confirmation from the user 104 that a retrieved user ID corresponds to the user 104. The customized exercise routine 516 may have been previously prescribed and maintained in the user profile store 114, or it may comprise a modified exercise routine. When the user 104 is ready to begin the customized exercise routine 516, he/she may select (e.g., via touch input to the UI 500) a "Begin" button 518 to initiate the customized exercise routine 516.

In some embodiments, the UI 500 may notify the user 104 that the sensors 314 of the networked fitness machine 102 will continually monitor his/her performance during the customized exercise routine 516. The UI 500 may also inform the user 104 that a workout summary will be uploaded to his/her user profile in the user profile store 114 after completion or termination of the customized exercise routine 516.

Phase II

When Phase I (Pre-Training) is complete, the networked fitness machine 102 may proceed to Phase II where the user 104 may be instructed to perform one or more warm up stretches. The output devices 308 may facilitate instructions to the user 104 on how to perform the warm up stretches, such as by showing images, video, and/or text via a display on how the stretch(es) should be performed, perhaps with audible instructions or signals. During the warm up stretching, the user 104 may manipulate any linear-based presentation (e.g., video) by pausing, rewinding, fast-forwarding, stopping, skipping, or other suitable UI controls provided on a display or another input device 306 (e.g., remote control, voice, etc.). The networked fitness machine 102 may instruct the user 104 to perform one or more dynamic stretches for a recommended number of times, and may continually monitor the user 104 via the one or more camera-based sensors (e.g., the camera-based sensor 510) to determine an exercise performance condition including the pose of the user 104 to evaluate whether the user 104 is performing the stretches correctly and/or for the recommended number of times. The user 104 may request more stretches from the networked fitness machine 102, or the user 104 may skip over certain ones of the stretches.

A warm up routine may begin after the user 104 has completed the warm up stretches. The warm up routine may include exercising at a moderate pace (e.g., walking, jogging, etc.) to achieve proper vital levels (e.g., heart rate, respiratory rate, etc.). During the warm up routine, the camera-based sensor 510 may capture movements of the user 104 to determine exercise performance conditions (e.g., body form, pace, etc.) in order to evaluate walking/running form. The sensors 314 may monitor other vitals, such as hydration, heart rate, and the like, to detect any concerns. External sensors may be used to may detect exercise performance conditions involving weight distribution on the feet of the user 104 to detect any potential concerns with how the user 104 is distributing weight during the warm up routine.

When the user 104 has reached target levels (e.g., 60%-80% of a predetermined heart rate level for exercise), the networked fitness machine 102 may ask the user 104, via the output device(s) 308, if the user 104 is ready to begin the exercise routine and/or inform the user 104 that his/her exercise routine will start. The user 104 may specify that they are not ready, and the networked fitness machine 102 may provide the user 104 with more time to get ready. The user 104 may stop the program entirely at any point in time. If the user 104 stops the program at any time, any data that has been captured by the sensors 314 may be uploaded to the server(s) 108(1)-(N) and stored in the user profile store 114 as part of a workout history of the user's profile.

The user 104 may be asked whether they would like music, video media, a competitor, and/or scenery while he/she exercises. The output device(s) 308 may be configured to provide the aforementioned functions to the user 104. In some embodiments, music may be streamed from other computing devices 312, such as the client device(s) 106(1)-(P), via Bluetooth®, for example. Video media may be presented in the form of a cable television signal or streamed video media from the other computing devices 312 including but not limited to Internet feeds, such as YouTube® or Netflix®.

Phase III

When the exercise routine begins, the user 104 starts exercising according to the exercise routine prescribed by the networked fitness machine 102. If Phase II (as described above) is skipped or omitted, the prescribed exercise routine of Phase III may include a warm-up portion that may or may not be "transparent" to the user 104. For example, the exercise routine may slowly ramp up to a "full speed" exercise routine by seamlessly transitioning through a warm-up phase. The user 104 may be notified of the warm-up phase before or during the ramp up period, or the system may not provide any notification to the user 104 such that the user 104 may be more or less unaware of the occurrence of a warm-up phase.

The exercise routine may comprise a steady or variable pace or speed, resistance, and/or incline over a prescribed duration of time. During the exercise routine, the networked fitness machine 102 may continuously monitor the user 104 with the sensors 314. For example, vital information may be monitored over the course of the exercise routine. Additionally, or alternatively, movements of the user 104 may collected by the camera-based sensor 510. For example, body form (e.g., running form) may be monitored by determining the angle or flex of the user's arms, the lateral swing of the user's limbs, angle of the user's head, contact of the user's foot with a running/walking surface, and/or whether the user's torso is erect or lordotic. The camera-based sensor 510 may also be configured to detect and interpret muscle images to determine how tense or relaxed the user's neck, arms, shoulders, and/or hands are while exercising.

A display may constantly, or periodically, display information regarding the sensed vital information of the user 104, such as heart rate, oxygen level, hydration level, and the like. In some embodiments, color coding (e.g., red, yellow, or green) may be utilized on a display to indicate an evaluation of exercise performance conditions of the user. The determination of appropriate vital levels may be based on a performance goal of the user 104, and/or an injury prevention metric.

In some embodiments, the networked fitness machine 102 may be configured to vary the speed, resistance, incline, decline, and/or duration to help the user 104 achieve target levels of performance or to prevent injury. For example, if a prescribed exercise routine was originally designed to burn a predetermined number of calories or achieve a target heart rate for the user 104, and the networked fitness machine 102, via the sensors 314, may determine that the user 104 will not achieve target performance levels with the originally prescribed routine, and may adjust speed, resistance, incline, and/or duration of the exercise routine, or otherwise dynamically modify the prescribed exercise routine to help the user 104 achieve goals, or to minimize risk of injury. For example, the camera-based sensor 510 may interpret movements of the user 104 to indicate an exercise performance condition that the user 104 is running with a certain body form that indicates fatigue. If the user 104 does not correct their body form after a predetermined time following an instruction to correct the user's running form, the networked fitness machine 102 may slow the speed, resistance, incline, and/or duration to minimize the risk of injury to the user 104.

Phase IV

When the customized exercise routine 516 is completed, the networked fitness machine 102 may initiate a cool down program. The cool down program may reduce the speed, resistance, and/or incline in order to reduce the heart rate of the user 104 to a level that is close to the resting heart rate of the user 104 measured during Phase I. In some embodiments, a display may present a video, graphics, or images of cool down stretches recommended for the user 104 to cool down. Other optional cool down programs may be presented to the user 104 for selection, such as sitting and performing static stretches, walking around and hydrating, or other suitable cool down methods.

The cool down program may be implemented similarly to the warm up program in that a display may present audio and video, images, graphics, etc., and the user 104 may pause, skip, rewind, and the like, to control the cool down presentation. Furthermore, the camera-based sensor 510 may collect image data of the user 104 when stretching to determine exercise performance conditions on body form and number of repetitions. This allows the networked fitness machine 102 to provide constructive feedback for the user 104 to correct body form, for example, if stretches are being performed incorrectly.

Phase V

An end routine may be implemented after cool down that shows a summary of important information via a display of the networked fitness machine 102. In some embodiments, the summary may be uploaded to the cloud (i.e., the server(s) 108(1)-(N)) and/or sent to other computing devices or accounts of the user 104, such as the client device(s) 106(1)-(P) or the user's e-mail, social networking account, and so on. The summary may include, but is not limited to, distance traveled, speed, calories burned, pace, and vital information measured during the exercise routine. Information such as speed, pace, and vital measurements may be presented as a graph (i.e., line graph) over the duration of the workout, and/or presented as average values. The summary may be presented via any suitable device and may give the user 104 the option to select a link for more detailed information containing charts, graphs, tables, etc.

The end routine may further involve asking the user 104 a series of questions, for example a display of the networked fitness machine 102, or via the client device(s) 106(1)-(P). The questions may include, but are not limited to, the following: (a) How do you feel after the workout?; (b) How would you rate the exercise routine?; (c) What went well or not so well with the workout? Answers may be selected from multiple choice options for efficiency purposes.

In some embodiments, the summary may highlight what went well during the exercise routine, such as distance, speed, calories burned, stance, pace, vital information, and the like. The summary may further indicate areas for improvement to be attempted during the next exercise routine.

In some embodiments, a short video or other suitable type of presentation may be shown to the user regarding what will be covered in the next exercise routine so that the user 104 may mentally prepare for the next exercise routine. The presentation of the next exercise routine may provide information on the distance, speed, pace, and/or duration to be covered in the next exercise routine. The summary may further give general or specific recommendations for the user 104 to act on in between exercise routines, such as to hydrate properly, eat a proper diet, or practice a running technique to improve running form.

In some embodiments, the summary may show progress made toward an overall goal. An avatar may be generated at the end of the exercise routine to reflect the accomplishments of the user 104 and it may be compared to a previous or initial avatar to indicate progress. In some embodiments, the networked fitness machine 102 may schedule a date and time for the next exercise routine, if it is not already scheduled, and add the scheduled routine to a calendar maintained by the user 104. Additionally, or alternatively, scheduling is performed from the server(s) 108(1)-(N) and the client device(s) 106(1)-(P) of the user 104, such as when the user 104 wants to leave immediately following the workout and take care of scheduling at a later time.

All information collected during the workout, whether the workout was completed, or whether the user 104 quit or aborted the workout, is uploaded to the server(s) 108(1)-(N) and stored in the user profile store 114. Information uploaded to the cloud may include, but is not limited to, vital measurements, image data, videos of the exercise routine, or any other suitable information. A workout history for the user 104 may be built over time to show fitness performance data that may be analyzed over time to identify trends, or other useful statistics that the user 104 may find valuable. The user 104 may share the uploaded information via social networking sites, with a health care professional, personal trainer, coach, insurance company, or the like.

Example Processes

Figure 6:
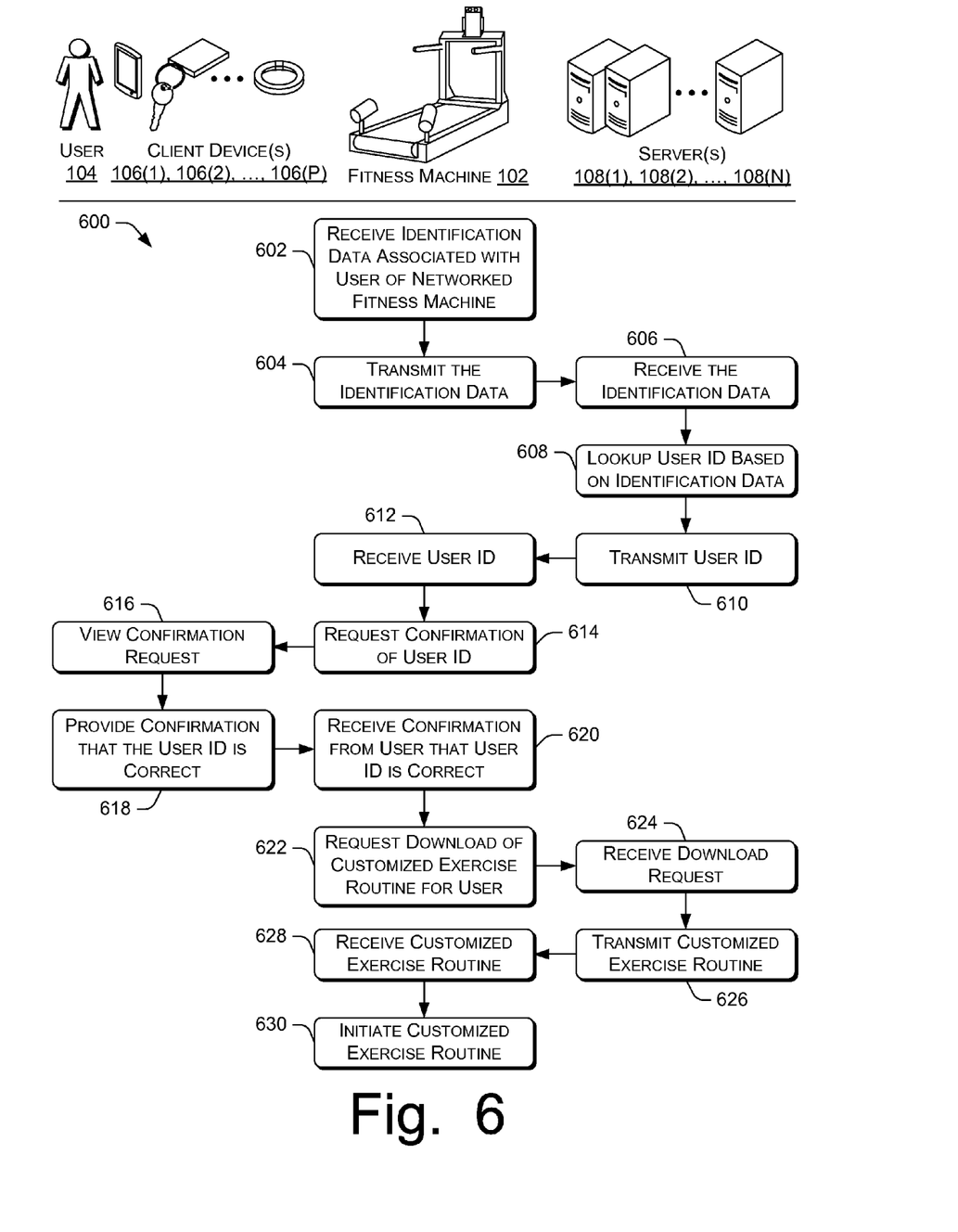
FIG. 6 is a flow diagram of an illustrative process of recognizing a user on a networked fitness machine to initiate a customized exercise routine.

FIG. 6 is a flow diagram of an illustrative process of recognizing a user 104 on a networked fitness machine 102 to initiate a customized exercise routine. The process is illustrated as a collection of blocks in a logical flow graph, which represent a sequence of operations that can be implemented in hardware, software, or a combination thereof. In the context of software, the blocks represent computer-executable instructions that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process.

For discussion purposes, the process 600 is described with reference to the networked fitness machine 102 of FIG. 3, and specifically with reference to the identification module 318, the authorization module 320, and the download/upload module 322. Although the process 600 is shown in reference to example steps to be carried out by the client device(s) 106(1)-(P), the fitness machine 102, and the server(s) 108(1)-(N), it is to be appreciated that, in instances where the fitness machine 102 is not part of the networked fitness system 111, the steps of the process 600 that are shown in association with the fitness machine 102 may be performed by any suitable device(s) (e.g., the client device(s) 106(1)-(P)) that constitute the networked fitness system 111.

At 602, the networked fitness machine 102 may receive identification data 208 that is associated with a user 104 of the networked fitness machine 102. For example, a unique device identifier of a client device 106 may be received at the networked fitness machine 102, as described above, or the camera-based sensor 510 may detect image data of the user's face for face detection, and so forth. Any suitable way of receiving unique identification data 208 associated with the user 104 may be used without changing the basic characteristics of the system.

At 604, the identification module 318 may cause the identification data 208 to be transmitted to one or more remotely located servers, such as the server(s) 108(1)-(N). At 606, the server(s) 108(1)-(N) may receive the identification data 208, and use the identification data 208 to lookup or otherwise locate a user ID at 608 that corresponds to the identification data 208. For example, a database of user IDs may be maintained in the user profile store 114 and associated with one or more forms of identification data 208, such as facial images of the user 104, device identifiers (e.g., IP addresses) of the client device(s) 106(1)-(P), and the like.

At 610, the server(s) 108(1)-(N) may transmit the retrieved user ID to the networked fitness machine 102, and, at 612, the user ID is received at the networked fitness machine 102. At 614, the authorization module 320 may request that the user 104 confirm that the user ID is correct (i.e., that the user ID corresponds to the user 104). In some cases, a user 104 may have been mistakenly identified, such as when a client device 106 is stolen and used by an unauthorized user.

At 616, the confirmation request is provided to the user 104 and viewed by the user 104, such as via a display of the networked fitness machine 102. At 618, the user 104 may confirm that the user ID is correct. For example, the user 104 may provide a "yes" or "no" input to the networked fitness machine 102. Additionally, or alternatively, the user 104 may provide security credentials (e.g., password, biometrics, answer to security question, etc.) as a form of providing the confirmation at 618 with an added layer of security.

At 620, the authorization module 320 may receive the confirmation from the user, and automatically proceed to 622 where the download/upload module 322 requests to download a customized exercise routine, such as the customized exercise routine 516, for the user 104. At 624, the server(s) 108(1)-(N) may receive the request from the download/upload module 322, and, at 626, the requested customized exercise routine 626 may be transmitted back to the networked fitness machine 102. In some embodiments, the server(s) 108(1)-(N) may perform the authorization process of the user 104, such as by receiving the security credentials of the user 104 prior to transmitting the customized exercise routine at 626.

At 628, the download/upload module 322 may receive the customized exercise routine. At 630, the networked fitness machine 102 may initiate the customized exercise routine. In some embodiments, the initiation at 630 is automatically performed by the networked fitness machine 102. In yet other embodiments, the user 104 is requested to provide input (e.g., via the "Begin" button 518) in order to initiate the customized exercise routine at 630.

The environment and individual elements described herein may of course include many other logical, programmatic, and physical components, of which those shown in the accompanying figures are merely examples that are related to the discussion herein.

Other architectures may be used to implement the described functionality, and are intended to be within the scope of this disclosure. Furthermore, although specific distributions of responsibilities are defined above for purposes of discussion, the various functions and responsibilities might be distributed and divided in different ways, depending on circumstances.

CONCLUSION

In closing, although the various embodiments have been described in language specific to structural features and/or methodological acts, it is to be understood that the subject matter defined in the appended representations is not necessarily limited to the specific features or acts described. Rather, the specific features and acts are disclosed as example forms of implementing the claimed subject matter.

The invention claimed is:

1. A method of recognizing a user via a networked fitness system to initiate a customized exercise routine, the method comprising:
    receiving, at the networked fitness system, identification data associated with the user;
    transmitting, by the networked fitness system, the identification data over a network to one or more remotely located servers;
    receiving, at the networked fitness system, a user identification (ID) from the one or more remotely located servers at least partly in response to the transmitting the identification data;
    receiving, at the networked fitness system, a confirmation from the user that the user ID corresponds to the user;
    automatically downloading, at least partly in response to the receiving the confirmation, a customized exercise routine associated with the user from the one or more remotely located servers;
    detecting, by one or more sensors of the networked fitness system, current vital measurements about the user;
    modifying the customized exercise routine based at least in part on the current vital measurements detected by the one or more sensors to generate a modified exercise routine; and
    initiating the modified exercise routine by the networked fitness system.

2. The method of claim 1, wherein the receiving the identification data comprises receiving a unique device identifier from at least one of a mobile phone, a key fob, a fitness tracking device, or a thumb drive.

3. The method of claim 1, wherein the identification data comprises image data of a face of the user obtained by a camera-based sensor of the networked fitness system, and wherein the user ID is located based on face recognition using the image data of the face of the user.

4. The method of claim 1, wherein the confirmation received from the user comprises one or more security credentials associated with the user.

5. The method of claim 1, wherein the receiving the identification data comprises receiving the identification data wirelessly from a mobile device.

6. The method of claim 5, further comprising establishing a handshake between the mobile device and the networked fitness system upon the receiving the identification data.

7. The method of claim 1, further comprising, receiving, at least partly in response to the receiving the confirmation:
 information about the user obtained from an online user profile; and
 an avatar of the user that is representative of a state of fitness of the user at a time in the past.

8. The method of claim 1, further comprising, receiving, prior to the automatically downloading the customized exercise routine, one or more answers from the user in response to a subjective feedback survey regarding recent activities or current health of the user.

9. The method of claim 1, further comprising automatically uploading a workout summary to the one or more remotely located servers after completion or termination of the modified exercise routine.

10. A networked fitness system comprising:
 one or more processors;
 one or more sensors configured to detect vital measurements; and
 one or more memories maintaining modules executable by the one or more processors, the modules comprising:
  an identification module to:
   receive identification data associated with a user, and
   cause transmission of the identification data over a network to one or more remotely located servers,
  an authorization module to
   receive a user identification (ID) from the one or more remotely located servers over the network at least partly in response to the transmission of the identification data; and
  a download module to:
   automatically download a customized exercise routine associated with the user from the one or more remotely located servers,
   modify the customized exercise routine based at least in part on current vital measurements about the user detected by the one or more sensors to generate a modified exercise routine, and
   initiate the modified exercise routine by the networked fitness system.

11. The networked fitness system of claim 10, wherein the identification data comprises a unique device identifier received from at least one of a mobile phone, a key fob, a fitness tracking device, or a thumb drive.

12. The networked fitness system of claim 10, further comprising a camera-based sensor, and wherein the identification data comprises image data of a face of the user obtained by the camera-based sensor, and wherein the user ID is located based on face recognition using the image data of the face of the user.

13. The networked fitness system of claim 10, wherein the authorization module is further configured to receive one or more security credentials associated with the user as a confirmation that the user ID corresponds to the user.

14. The networked fitness system of claim 10, wherein the download module is further configured to receive:
 information about the user obtained from an online user profile; and
 an avatar of the user that is representative of a state of fitness of the user at a time in the past.

15. One or more non-transitory computer-readable media storing computer-executable instructions that, when executed on one or more processors, perform acts comprising:
 receiving, at a networked fitness system, identification data associated with a user of the networked fitness system;
 transmitting, by the networked fitness system, the identification data over a network to one or more remotely located servers;
 receiving, at the networked fitness system, a user identification (ID) from the one or more remotely located servers at least partly in response to the transmitting the identification data;
 automatically downloading a customized exercise routine associated with the user from the one or more remotely located servers;
 detecting, by one or more sensors of the networked fitness system, current vital measurements about the user;
 modifying the customized exercise routine based at least in part on the current vital measurements detected by the one or more sensors to generate a modified exercise routine; and
 initiating the modified exercise routine by the networked fitness system.

16. The one or more non-transitory computer-readable media of claim 15, wherein the receiving the identification data comprises receiving a unique device identifier from at least one of a mobile phone, a key fob, a fitness tracking device, or a thumb drive.

17. The one or more non-transitory computer-readable media of claim 15, the acts further comprising receiving a confirmation from the user that the user ID corresponds to the user, the confirmation comprising one or more security credentials associated with the user.

18. The one or more non-transitory computer-readable media of claim 15, the acts further comprising automatically uploading a workout summary to the one or more remotely located servers after completion or termination of the modified exercise routine.

19. The one or more non-transitory computer-readable media of claim 15, the acts further comprising receiving:
 information about the user obtained from an online user profile; and
 an avatar of the user that is representative of a state of fitness of the user at a time in the past.

20. The one or more non-transitory computer-readable media of claim 15, the acts further comprising receiving, prior to the automatically downloading the customized exercise routine, one or more answers from the user in response to a subjective feedback survey regarding recent activities or current health of the user.

* * * * *